(12) United States Patent
Bomkamp

(10) Patent No.: US 8,192,502 B2
(45) Date of Patent: Jun. 5, 2012

(54) PAIN REDUCING AND ELIMINATING PROSTHESIS SOCKET DEVICE

(76) Inventor: Katherine Emily Bomkamp, Colfax, NC (US)

(*) Notice: Subject to any disclaimer, the term of this patent is extended or adjusted under 35 U.S.C. 154(b) by 217 days.

(21) Appl. No.: 12/701,601

(22) Filed: Feb. 7, 2010

(65) Prior Publication Data

US 2010/0204805 A1    Aug. 12, 2010

Related U.S. Application Data

(60) Provisional application No. 61/150,792, filed on Feb. 8, 2009.

(51) Int. Cl.
*A61F 2/60* (2006.01)
*A61F 2/78* (2006.01)

(52) U.S. Cl. .......................................................... 623/33

(58) Field of Classification Search .............. 623/32–37, 623/57; 602/2, 62–63
See application file for complete search history.

(56) References Cited

U.S. PATENT DOCUMENTS

| | | | | |
|---|---|---|---|---|
| 3,751,733 A * | 8/1973 | Fletcher et al. | ................. | 623/24 |
| 5,413,611 A * | 5/1995 | Haslam et al. | ................... | 623/25 |
| 2009/0132056 A1 * | 5/2009 | Kania | ............................. | 623/36 |
| 2009/0227924 A1 * | 9/2009 | Conrad et al. | .................... | 602/2 |
| 2009/0271000 A1 * | 10/2009 | Altobelli et al. | ................. | 623/37 |

* cited by examiner

*Primary Examiner* — Bruce E Snow
(74) *Attorney, Agent, or Firm* — Andrew D. Wright; Roberts Mlotkowski Safran & Cole, P.C.

(57) ABSTRACT

The present invention is a general pain and phantom pain reducing and eliminating prosthesis socket device for an amputee user with an amputated body part. The device has a core socket and a silicon socket cup placed inside the core socket to receive the amputated body part and a wireless transmitter Fob that includes a programmable microprocessor, a wireless radio transmitter IC board, an adjustable potentiometer, a momentary on and off switch, a light emitting diode and a DC power source. The wireless receiver module also includes a wireless processor printed circuit board, a battery and power supply, a thermocouple temperature probe and a heating coil.

20 Claims, 5 Drawing Sheets

US 8,192,502 B2

PAIN REDUCING AND ELIMINATING PROSTHESIS SOCKET DEVICE

This application claims priority to U.S. Provisional Application 61/150,792 filed on Feb. 8, 2009, the entire disclosure of which is incorporated by reference.

TECHNICAL FIELD & BACKGROUND

The present invention generally relates to a pain reducing and eliminating prosthesis socket device. More specifically, the invention is a pain reducing and eliminating prosthesis socket device that reduces and eliminates phantom pain.

It is an object of the invention to provide a pain reducing and eliminating prosthesis socket device that utilizes heat to reduce general and phantom pain.

It is also an object of the invention to provide a pain reducing and eliminating prosthesis socket device that incorporates an overall electrical circuit design and state of the art wireless control system to reduce general and phantom pain.

What is really needed is a pain reducing and eliminating prosthesis socket device that provides heat to the point of contact between an amputee's body part and the prosthesis socket device that can eliminate or reduce general and phantom pain experienced by the amputee that would wear the prosthesis socket.

BRIEF DESCRIPTION OF THE DRAWINGS

The present invention will be described by way of exemplary embodiments, but not limitations, illustrated in the accompanying drawings in which like references denote similar elements, and in which.

DETAILED DESCRIPTION OF ILLUSTRATIVE EMBODIMENTS

Various aspects of the illustrative embodiments will be described using terms commonly employed by those skilled in the art to convey the substance of their work to others skilled in the art. However, it will be apparent to those skilled in the art that the present invention may be practiced with only some of the described aspects. For purposes of explanation, specific numbers, materials and configurations are set forth in order to provide a thorough understanding of the illustrative embodiments. However, it will be apparent to one skilled in the art that the present invention may be practiced without the specific details. In other instances, well-known features are omitted or simplified in order not to obscure the illustrative embodiments.

Various operations will be described as multiple discrete operations, in turn, in a manner that is most helpful in understanding the present invention, however, the order of description should not be construed as to imply that these operations are necessarily order dependent. In particular, these operations need not be performed in the order of presentation.

The phrase "in one embodiment" is used repeatedly. The phrase generally does not refer to the same embodiment, however, it may. The terms "comprising", "having" and "including" are synonymous, unless the context dictates otherwise.

Figure 1:
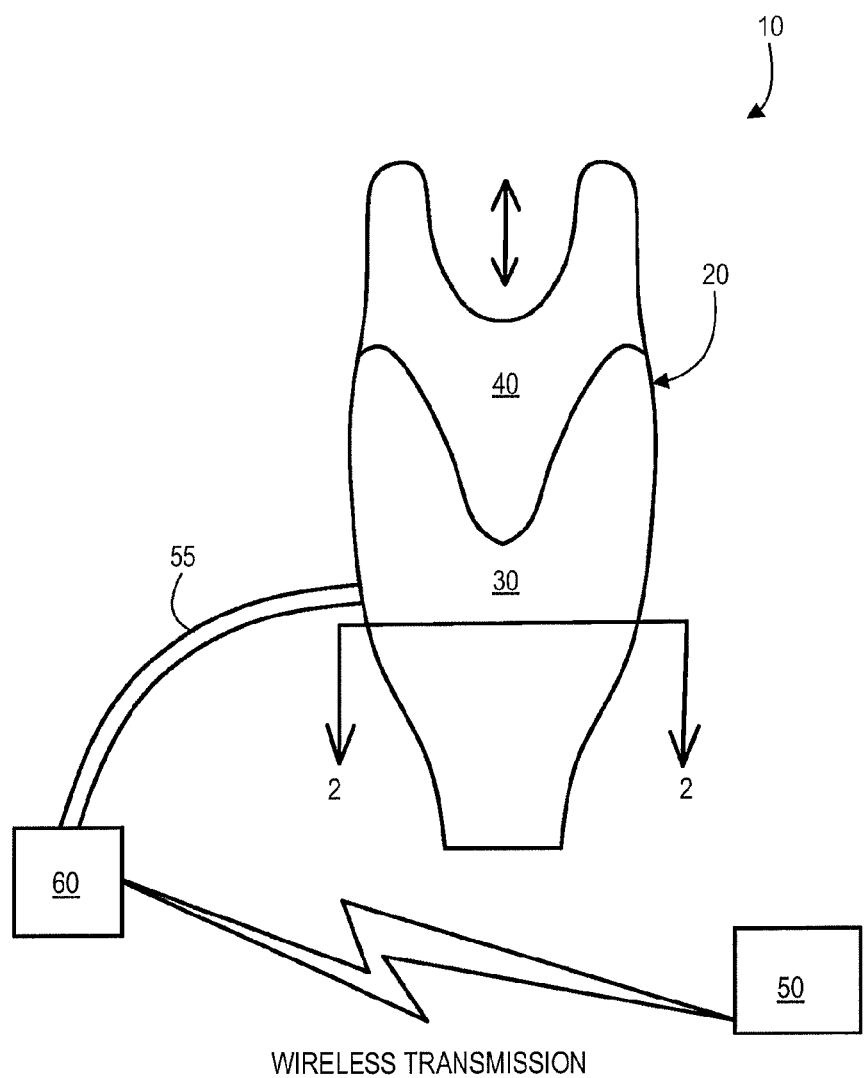
FIG. 1 illustrates a front perspective view of a pain reducing and eliminating prosthesis socket device, in accordance with one embodiment of the present invention.

FIG. 1 is a front perspective view of a pain reducing and eliminating prosthesis socket device 10 for an amputee user with an amputated body part (not shown). The pain reducing and eliminating prosthesis socket device 10 is designed to be used as a below the knee device, although this is only one possible embodiment and the device 10 is not limited to just this embodiment. The pain reducing and eliminating prosthesis socket device 10 is made up of a prosthesis portion 20 that has a core socket 30 and a silicon socket cup 40 placed inside the core socket 30 to receive the user's amputated body part. The silicon socket cup 40 is set in-between the amputee's body part and the core socket 30. More details on the core socket 30 and socket cup 40 are discussed in the FIG. 2 description.

FIG. 1 also illustrates a wireless receiver module 60 that houses some of the electronics components associated with the pain reducing and eliminating prosthesis socket device 10. These electronic components control some of the features of the pain reducing and eliminating prosthesis socket device 10. There is also an electronics cable or wiring 55 that transmits electrical information to and from the wireless receiver module 60 and serves as an electrical conduit between the receiver module 60 and the prosthesis portion 20. There is also a wireless transmitter Fob 50 that is in wireless communication with the wireless receiver module 60. The wireless transmitter Fob 50 is physically small and wearable and is capable of transmitting serial data a short distance to the wireless receiver module 60 worn by the user amputee. The wireless transmitter Fob 50, the wireless receiver module 60 and the electrical and wireless components associated with the transmitter Fob 50 and the receiver module 60 are all well-known to those schooled in the art and are discussed in more detail in the FIG. 3 and FIG. 4 descriptions.

Figure 2:
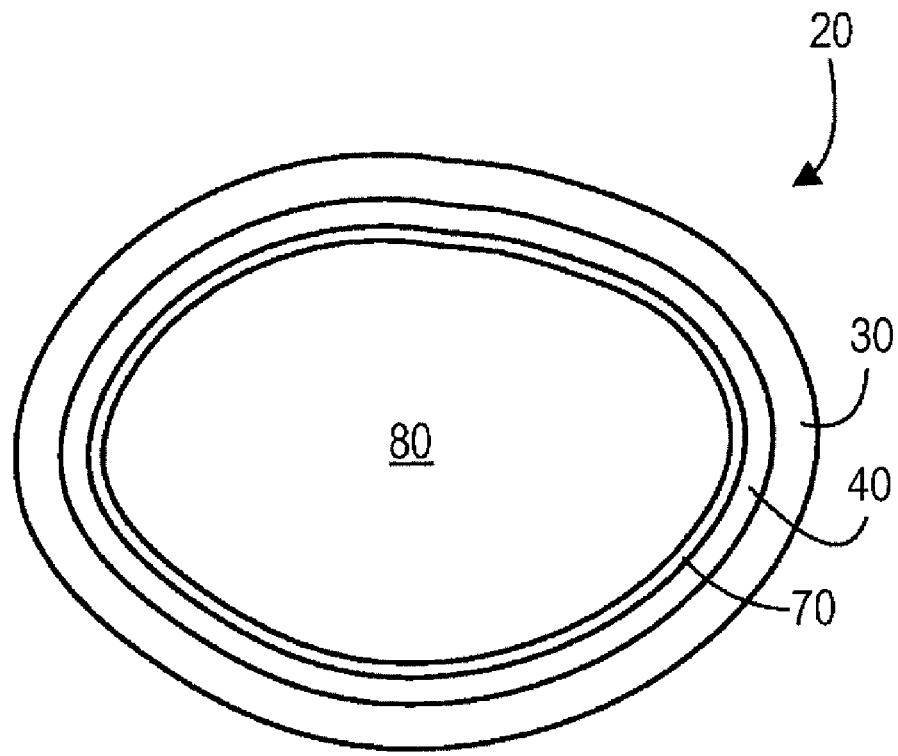
FIG. 2 illustrates a cross-sectional perspective view along line 2-2 of FIG. 1, of a pain reducing and eliminating prosthesis socket device, in accordance with one embodiment of the present invention.

FIG. 2 illustrates a cross-sectional view of the prosthesis portion 20 of the pain reducing and eliminating prosthesis socket device 10. As previously indicated, the prosthesis portion 20 has a core socket 30, which is made of carbon fiberglass, and a socket cup 40, which is made of silicon. The core socket 30 is made of carbon fiberglass because of the excellent insulating capabilities of carbon fiberglass, which is commonly used in other insulating applications. The socket cup 40 is made of Pro-Flex™, which is a silicone based material chosen for its high tolerance for heat, which is also used for other high heat tolerance applications. Both carbon fiberglass and Pro-Flex are well known to those schooled in the art. The inner most layer of the prosthesis portion 20 is a laminate layer 70, which is between the socket cup 40 and the interior of the socket 80 or amputee's body part. A heating coil 180 (see FIG. 3 description) is also embedded between the socket cup 40 and the laminate 70 and allows the heating coil 180 to be installed easily. The laminate 70 is also thick enough to ensure an amputee user's comfort while being worn. The heating coil 180 is further discussed at much greater length in addition to the other electrical components of the pain reducing and eliminating prosthesis socket device 10 in the FIG. 3 description. The pain reducing and eliminating prosthesis socket device 10 is designed to address pain and specifically phantom pain with heat via the heating coil 180. However, the pain reducing and eliminating prosthesis socket device 10 can also include possible additional features such as a stump massage function, a stump skin care lotion dispenser or other external features (all of which are not shown) to further address an amputee user's comfort. Future plans also include adding variable switches and resistors to incorporate a massage on/off switch, a massage intensity switch and massage duration timers (all of which are also not shown).

Figure 3:
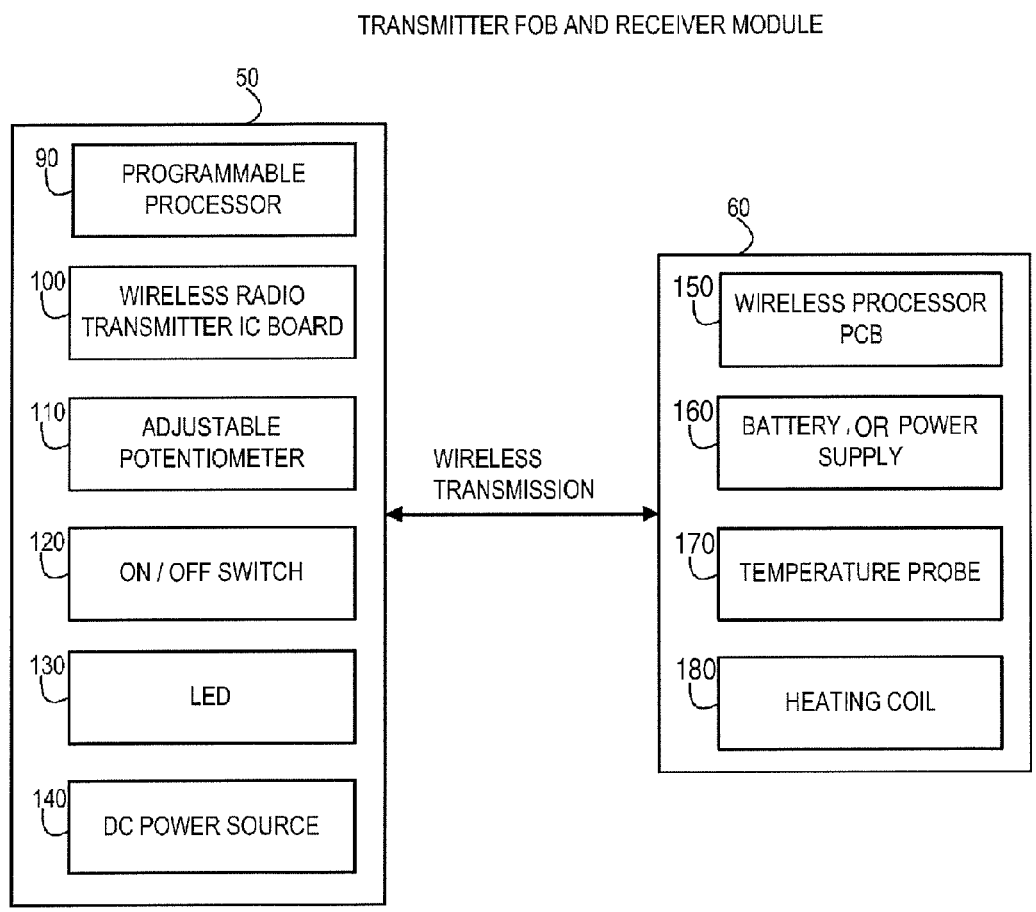
FIG. 3 illustrates a diagram of a transmitter Fob and a receiver module of a pain reducing and eliminating prosthesis socket device, in accordance with one embodiment of the present invention.

FIG. 3 illustrates the electrical and wireless components of the pain reducing and eliminating prosthesis socket device 10. As previously mentioned in the FIG. 1 and FIG. 2 descriptions, all of the wireless and electrical components associated with the pain reducing and eliminating prosthesis socket device 10 are utilized in wireless transmitter Fob 50 and the wireless receiver module 60. Both the wireless transmitter Fob 50, the wireless receiver module 60 and their electrical and wireless components are well known to persons who are skilled in the art.

The wireless transmitter Fob 50 includes a programmable microprocessor 90, a wireless radio transmitter IC board 100, an adjustable potentiometer 110, a momentary on and off switch 120, a light emitting diode 130 and a DC power source 140. The wireless radio transmitter IC board 100 operates in the 434 MHz range, the adjustable potentiometer 110 is 5 kilohm and the power source is a 12 volt DC power source, although the wireless transmitter Fob 50 is not limited to the 434 MHz range, 5 kilohms and use of only a 12V DC power source, as other quantities can also be used. The components used to construct the transmitter fob 50 are currently available and are considered off-the-shelf electronic items.

The Fob's microprocessor 90 is the Arduino Mini Pro Board manufactured by Sparkfun Electronics, operating at 16 MHz and 5 volts DC. The indicator LED 130 and momentary switch (120) are very common. The microprocessor programming language is the open-source Arduino processing language. The transmitter IC board 100 is an industry-standard radio frequency (RF) SAW transmitter similar to those used in car alarms and keyless entry Fobs. This unit is made by the Holy Stone Enterprise Co., LTD.

The 5 kilohm slide or variable potentiometer 110 is available from multiple sources and can be a slide or round version, depending on availability and space requirements. The 12 volt DC power source 140 is a common, replaceable single N-size battery (battery not shown) and the LEDs 130 are switch and indicator LEDs and are very common components available from a variety of suppliers. The transmitter Fob 50 is also not limited to the brand names and makes indicated, as comparable electrical and wireless components can be used as well.

The momentary switch 120 connects the 12 volt power source 140 to both the transmitter Fob 50 and the microprocessor 90. It allows the microprocessor 90 to begin a boot process to start the onboard microprocessor functions. At this time, the microprocessor's onboard voltage regulator (not shown) reduces the 12 volts DC to a 5 volt DC supply and provides a regulated voltage from its 5 VDC output pin (not shown). The 5 volt supply is connected to one side of the adjustable potentiometer 110, which has 3 pins (not shown). The center pin of the potentiometer (not shown) is connected to the analog 0 pin of the microprocessor (not shown) to give a position or "sense" line. This input is an analog value that can range anywhere from 0 to 5 volts, depending on the resistive position of the potentiometer 110. The last or third pin of the potentiometer (not shown) is connected to a common ground (not shown) that returns the current to the negative side of the 12 volt power source 140. This common ground is also connected to the wireless radio transmitter IC board 100 and the microprocessor 90. After the microprocessor 90 boots into its operating mode, it checks the DC voltage on the Analog 0 pin and converts the analog voltage into a digital numerical value that can range from 0 up to 255, depending on the position of the slider arm of the potentiometer 110. This value is now the new heat control setting that will be transmitted to the wireless receiver module 60. The microprocessor 90 is now able to transmit a continuous stream of data to the receiver module 60. This pin is connected to the data pin (both pins not shown) of the wireless radio transmitter board 100. The data transmitted by the transmitter Fob 50 is made up of 5 data transmitted byte types of information, all of which are described in FIG. 4 and the FIG. 4 description.

The wireless receiver module 60 of the pain reducing and eliminating prosthesis socket device 10 includes an Arduino microprocessor board, a wireless processor printed circuit board (PCB) 150, a battery or power supply 160, a thermocouple temperature probe 170 and a heating coil 180. Details of the processor PCB 150 are depicted and discussed in FIG. 5 and the FIG. 5 description. The wireless receiver module 60 uses a standard lithium-polymer Li—Po battery pack (not shown) as the battery and power supply 160. The Li—Po battery pack is commonly found in radio-controlled toys and also serves as an 11.1 volt power supply for both the heating coil 180 and the wireless microprocessor board 150 of the pain reducing and eliminating prosthesis socket device 10. The Li—Po battery pack has the ability to supply a large amount of current to the heating coil 180 as needed. However, due to the weight of the Li—Po battery pack in its current configuration, it is more desirable and it is the best mode to use a custom, lightweight, moldable battery pack as the battery and power supply 160. Both types of battery packs are well-known to those schooled in the art and the pain reducing and eliminating prosthesis socket device 10 is not limited to using only these types of battery packs.

A thermocouple temperature probe 170 is also utilized within the socket cup 40 of the pain reducing and eliminating prosthesis socket device 10. The thermocouple temperature probe 170 is a standard Type K chromel-alumel junction thermocouple used to measure temperature inside the socket cup 40. The pain reducing and eliminating prosthesis socket device 10 is not limited to using this type of thermocouple temperature probe 170. Multiple thermocouple temperature probes 170 can also be used to sense a larger area within the socket cup 40. The heating coil 180 used in the pain reducing and eliminating prosthesis socket device 10 is a piece of nickel-chromium wire (not shown) with a resistance that is low enough to heat quickly when power is applied to it. However, the nickel-chromium wire also has a small enough diameter to allow it to be woven into the silicone socket cup 40. The heating coil 180 also has a variable resistor (not shown) for specific heat point selection. This socket cup 40 with the heating coil 180, can be placed into the core socket 30 and prosthetic portion 20 without interfering with the amputee user's ability to use the pain reducing and eliminating prosthesis socket device 10. The heating coil 180 works based on the principles of thermal biofeedback from concentrated and controlled heat. The concentrated and controlled heat of the heating coil 180 works to stimulate severed nerve endings in the amputee body part and to force the brain to focus on the heat, rather than a missing body part that is no longer there.

The thermocouple temperature probe 170 and heating coil 180 are also well known to those schooled in the art.

Figure 4:
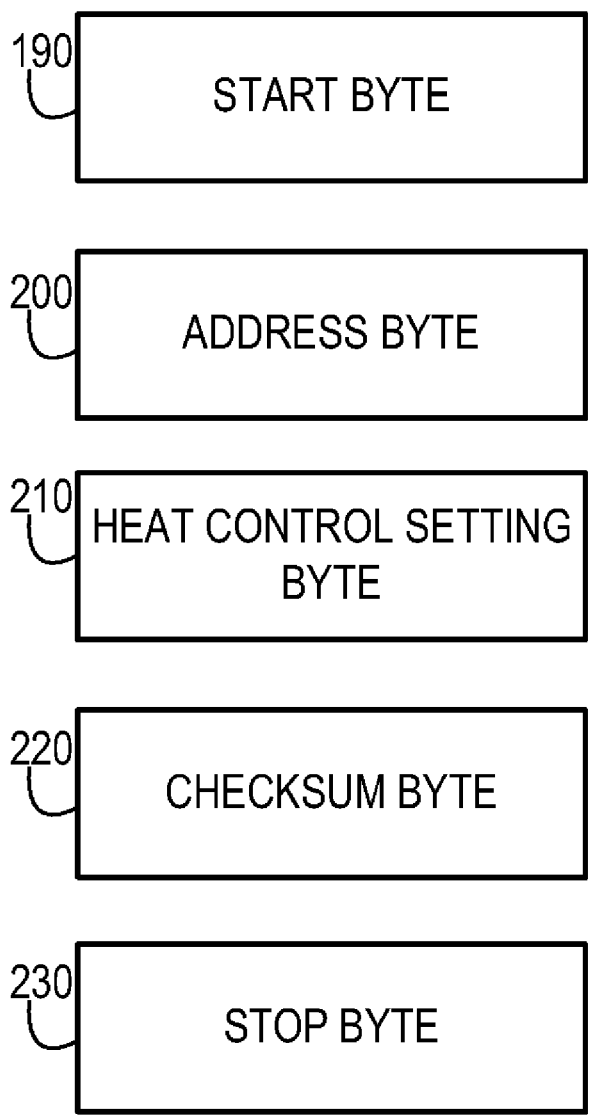
FIG. 4 illustrates a diagram of data transmitted byte types transmitted in the pain reducing and eliminating prosthesis socket device, in accordance with one embodiment of the present invention.

The wireless transmitter Fob 50 transmits wireless transmitter code information to the wireless receiver module 60 that is worn by the amputee, and the receiver module 60 decodes the code information to perform tasks from the wireless transmitter Fob 50. As depicted in FIG. 4, the wireless transmitter code information includes various data transmitted byte types such as a start byte 190, an address byte 200, a heat control setting byte 210, a checksum byte 220 and a stop byte 230.

The start byte 190 is a set of 8 bits of information that utilizes a string of alternating zeros and ones. This initial data string allows the wireless processor PCB 150 of the wireless receiver module 60 to begin locking onto the incoming wireless transmitted serial data stream, should a period of inactivity occur from the transmitter Fob 50, as will sometimes occur as a plan to save the battery life of the transmitter Fob 50. The address byte 200 is a preprogrammed address that will uniquely match the transmitter Fob 50 to its matched receiver module 60 if more than two pain reducing and eliminating prosthesis socket devices 10 operate in the same general area. This address byte 200 serves as a check on the receiving module 60 that will prevent one transmitter Fob 50 from accidentally sending wirelessly transmitted information to an unintended transmitter Fob 50 and pain reducing and eliminating prosthesis socket device 10. There is also a heat control setting byte 210 that indicates the digitized position of the heat control slider of the adjustable potentiometer 110. There is also a checksum byte 220, which is a numerical mathematical value generated by the transmitter programmable microprocessor 90 that allows the receiver module 60 to check if the address and heat control information received matches what was sent. The receiver module 60 gets the correct start byte 190 and the correct address byte 200 and will also verify a correct heat setting byte 210 that has been received by the use of the checksum byte 220. The stop byte 230 is a final byte in a transmitted serial data stream that lets the receiver module 60 knows it has reached the end of the serial data stream transmission and to stop processing any received serial data. The start byte 190, the address byte 200, the heat control setting byte 210, the checksum byte 220 and the stop byte 230 are all well known to those schooled in the art.

Figure 5:
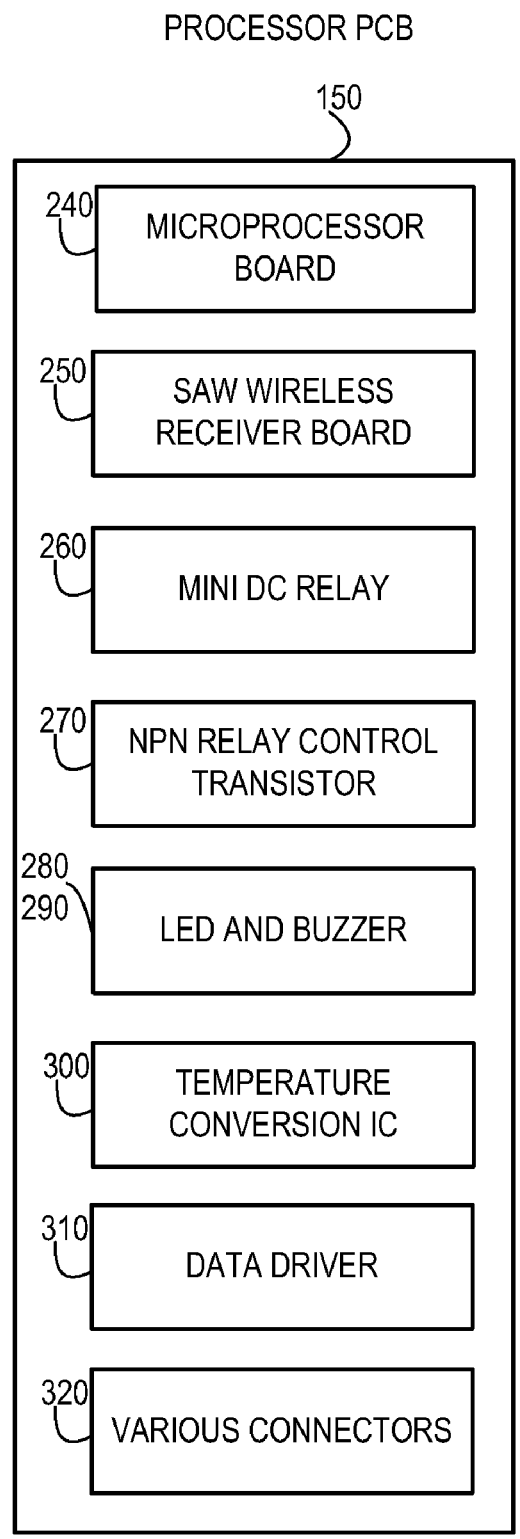
FIG. 5 illustrates a diagram of a wireless processor printed circuit board components, in accordance with one embodiment of the present invention.

FIG. 5 illustrates the components of the wireless processor PCB 150 used in wireless receiver module 60 and the pain reducing and eliminating prosthesis socket device 10. The processor PCB 150 utilizes a microprocessor board 240, a SAW wireless receiver board 250, a mini DC relay 260, a NPN relay control transistor 270, a power indicator LED 280, a buzzer 290, a temperature conversion IC 300, a data driver IC 310 and various connectors 320 to connect the thermocouple temperature probe 170 and the heating coil 180 wiring leads. The wireless processor board 150 is the main board of the pain reducing and eliminating prosthesis socket device 10 that continuously monitors the core socket temperature and regulates the voltage across the heater coil 180 so that the heat produced by the heater coil 180 will closely match the heat control temperature settings received from the transmitter Fob 50. It also alerts the user if any new heat control temperature settings transmitted to the processor PCB 150 have been updated. The processor PCB 150 uses an Arduino Mini Pro microprocessor board that operates at 16 MHz and uses a 5 volt supply voltage in the pain reducing and eliminating prosthesis socket device 10. The SAW wireless receiver board 250 used with the processor PCB 150 operates in the 434 MHz range and an AN594 temperature conversion IC is the temperature conversion IC 300 used. The SAW wireless receiver board 250 used is made by the Holy Stone Enterprise Co., LTD. and the rest of the components used are available through multiple electronics parts vendors. The wireless processor PCB 150 however, is not limited to using the SAW wireless receiver board 250 made by the Holy Stone Enterprise Co., LTD. and is not limited to using an AN594 temperature conversion IC. Also the wireless processor PCB 150 is not limited to using an Arduino Mini Pro microprocessor board as its microprocessor board 240 as well.

In the wireless processor PCB 150, a 11.1 volt battery's positive and ground leads (not shown) are connected to the SAW receiver board 250 through a standard, polarized, removable 2-pin connector (not shown). This type of connector allows for the removal and charging of the battery separately from the SAW receiver board 250 as needed. The ground lead connects to a common ground bus (not shown) on the wireless processor PCB 150 and the positive lead connects to both the microprocessor's 240 raw vcc pin (not shown) and to one side of the 5 volt mini DC relay's 260 normal open pin contacts (not shown). The microprocessor 240 boots into its normal pre-programmed operation of sensing the core socket temperature and opening and closing the relay contacts (not shown) to keep the heating coil 180 at a nominal start up temperature of 90 degrees. The SAW wireless receiver board 250 gets its power from the regulated 5 volt supply pin and will only transmit data to the microprocessor 240 if it is received at the correct frequency. If no activity is sensed on the microprocessor 240 RX receiver pin (not shown), the microprocessor 240 will simply continue to regulate the temperature of the core socket 30 at the pre-programmed initial 90 degree setting. If new heat control settings are transmitted to the receiver module 60 at the correct frequency, the microprocessor 240 will begin to process the incoming serial data and look for the correct start byte 190, then the correct address byte 200, then the heat control setting byte 210, the checksum byte 220 and the stop byte 230. If the microprocessor 240 determines that either the start byte 190 or the address byte 200 is incorrect, it will discard the entire data string and wait for a new start byte 190. If the microprocessor 240 gets the correct start byte 190 and correct address byte 200, it will then verify that the correct heat control setting byte 210 has been received by use of the checksum byte 220. If everything is correct, then the microprocessor 240 will store the new heat control setting, send a short duration voltage pulse to the buzzer 290 indicating that the data was received correctly and then open or close the relay to adjust the socket temperature to the new heat setting. Once the wireless signal ends, the microprocessor 240 will continue monitoring the socket temperature and compare it to the new heat setting until new information is sent.

The wireless receiver board 250 cannot connect directly to the microprocessor board's RX input pin (not shown) due to the limits of its current sourcing capability. Therefore it is necessary to use a data driver IC 310 between the microprocessor board's RX pin and the data pins of the receiver board 250 (not shown). This data driver IC 310 is the 74LS02 Quad, two-input NOR gate. The wireless receiver board's data pins interface with the RX line of the microprocessor 240 by using two of the available NOR gates in series. It is necessary to use a temperature conversion IC 300 between the thermocouple temperature probe 170 and the microprocessor 240. The temperature conversion IC 300 used for this voltage conversion is the AD5895AQ. This is a temperature conversion IC 300 produced by Analog Device, Inc. The conversion IC 300 draws its 5 volt DC supply from the microprocessor's 5 volt pin. The conversion IC's ground pin (not shown) is tied into the common ground on the wireless control processor PCB (not shown). The output pin of the AD5895AQ is connected to the microprocessor's analog 0 pin (not shown). The microprocessor 240 uses onboard programming to use this voltage to compare the core socket temperature to the stored heat set point transmitted to it from the wireless transmitter Fob 50.

One of the microprocessor's digital I/O pins interfaces with the base of one NPN transistor 270 to control the current flow to the heating coil 180. The collector of the transistor (not shown) is connected to the 5 volt supply of the microprocessor 240 through a 1000 Ohm resistor (not shown). The emitter of the transistor (not shown) is then tied to the positive input side of the DC relay 260. The ground or negative side of the relay (not shown) is tied to the ground rail (not shown). The microprocessor 240 controls the status of the transistor 270 to make it act as an on/off switch. The relay 260 can then be pulsed on or off as determined by the microprocessor 240. The large current flow needed by the heating coil 180 can safely pass through the copper switches located inside the enclosed relay 260. The microprocessor on the receiver board 240 operates until the power supply is disconnected. If the power is disconnected, the pain reducing and eliminating prosthesis socket device 10 will revert to the low temperature setting at startup.

While the present invention has been related in terms of the foregoing embodiments, those skilled in the art will recognize that the invention is not limited to the embodiments described. The present invention can be practiced with modification and alteration within the spirit and scope of the appended claims. Thus, the description is to be regarded as illustrative instead of restrictive on the present invention.

What is claimed is:

1. A phantom pain reducing and eliminating prosthesis socket device for an amputee user with an amputated body part wearing said device, comprising:
   a prosthesis portion with a core socket and a socket cup placed inside said core socket;
   a wireless transmitter that includes a programmable microprocessor and a wireless radio transmitter; and
   a wireless receiver module that includes a wireless processor printed circuit board, a battery or power supply, a temperature probe, and a heating coil;
   wherein the temperature probe and the heating coil are contained in the prosthesis portion;
   said wireless transmitter is configured to wirelessly transmit information to said wireless receiver module; and
   the wireless processor printed circuit board is configured to monitor a socket temperature detected by the temperature probe, compare the socket temperature to the information, and regulate a voltage across the heating coil based on the information.

2. The device according to claim 1, wherein said core socket is made of carbon fiberglass and said socket cup is made of silicon.

3. The device according to claim 1, wherein said processor board gets a correct start byte and address byte and will verify a correct heat control setting byte that has been received by use of a checksum byte.

4. The device according to claim 1, wherein said battery or power supply is one of a battery pack and a custom, lightweight and moldable battery pack.

5. The device according to claim 1, wherein said temperature probe comprises a plurality of temperature probes placed in said socket cup.

6. The device according to claim 1, wherein said temperature probe is a Type K chromel-alumel junction thermocouple used to measure temperature inside said socket cup.

7. The device according to claim 1, wherein said heating coil is embedded between said socket cup and a laminate that is inside said socket cup between said socket cup and said amputated body part when placed on the amputee.

8. The device according to claim 7, wherein said heating coil has a variable resistor for heat point selection.

9. The device according to claim 8, wherein said heating coil is made of heat resistive nickel-chromium wiring.

10. The device according to claim 1, wherein Bluetooth technology is used for said wireless transmitter to transmit said information to said wireless receiver module.

11. A pain reducing and eliminating prosthesis socket device for an amputee user with an amputated body part wearing said device, comprising:
    a prosthesis portion with a core socket and a socket cup placed inside said core socket;
    a wireless transmitter Fob that includes a programmable microprocessor, a wireless radio transmitter IC board, an adjustable potentiometer, a momentary on and off switch, a light emitting diode and a DC power source; and
    a wireless receiver module that includes a wireless processor printed circuit board, a battery or power supply, a thermocouple temperature probe and a heating coil, said wireless processor printed circuit board contains a microprocessor board, a SAW wireless receiver board, a mini DC relay, a NPN relay control transistor, a power indicator LED, a buzzer, a temperature conversion IC, a data driver IC and various connectors to connect said temperature probe and said heating coil leads;
    wherein said wireless transmitter Fob transmits wireless transmitter code information to said wireless receiver module that is worn by said amputee and said receiver module decodes said code information to perform tasks from said transmitter Fob; and
    said wireless transmitter code information includes a start byte, an address byte, a heat control setting byte, a checksum byte and a stop byte.

12. The device according to claim 11, wherein said core socket is made of carbon fiberglass and said socket cup is made of silicon.

13. The device according to claim 11, wherein said processor board gets a correct said start byte and said address byte and will verify a correct said heat control setting byte that has been received by use of said checksum byte.

14. The device according to claim 11, wherein said battery or power supply is one of a battery pack and a custom, lightweight and moldable battery pack.

15. The device according to claim 11, wherein said temperature probe comprises a plurality of temperature probes placed in said socket cup.

16. The device according to claim 11, wherein said thermocouple temperature probe is a Type K chromel-alumel junction thermocouple used to measure temperature inside said socket cup.

17. The device according to claim 11, wherein said heating coil is embedded between said socket cup and a laminate that is inside said socket cup between said socket cup and said amputated body part when placed on the amputee.

18. The device according to claim 17, wherein said heating coil has a variable resistor for heat point selection.

19. The device according to claim 18, wherein said heating coil is made of heat resistive nickel-chromium wiring.

20. The device according to claim 11, wherein Bluetooth technology is used for said wireless transmitter Fob to transmit said wireless transmitter code information to said wireless receiver module.

* * * * *